United States Patent [19]

Nozhnikov et al.

[11] 3,989,051
[45] Nov. 2, 1976

[54] APPARATUS FOR CURRENT PULSE ACTION UPON CENTRAL NERVOUS SYSTEM

[76] Inventors: Valentin Matveevich Nozhnikov, Krasnodarskaya ulitsa, 33, kv. 82; Eduard Mikhailovich Kastrubin, B. Pirogovskaya ulitsa, 29/31, kv. 41, both of Moscow, U.S.S.R.

[22] Filed: June 30, 1975

[21] Appl. No.: 591,697

Related U.S. Application Data

[63] Continuation of Ser. No. 510,624, Sept. 30, 1974, abandoned.

[52] U.S. Cl. .............................. 128/421; 128/1 C; 128/2.1 P; 128/410
[51] Int. Cl.² .............................................. A61B 1/34
[58] Field of Search ............... 128/1 C, 2.1 P, 2.1 R, 128/410, 419 R, 421, 422, 423

[56] References Cited
UNITED STATES PATENTS

| | | |
|---|---|---|
| 3,513,851 | 5/1970 | Smith et al. .......................... 128/422 |
| 3,518,986 | 7/1970 | Woods et al. ..................... 128/2.1 P |
| 3,521,641 | 7/1970 | Farensbach .......................... 128/1 C |
| 3,648,708 | 3/1972 | Haeri .................................. 128/1 C |
| 3,683,923 | 8/1972 | Anderson .......................... 128/2.1 P |
| 3,791,373 | 2/1974 | Winkler et al. ..................... 128/1 C |

Primary Examiner—William E. Kamm
Attorney, Agent, or Firm—Holman & Stern

[57] ABSTRACT

An apparatus for current pulse action upon the central nervous system, wherein current pulses are applied from a unit for rhythmic current pulse action upon the central nervous system of a patient, via a unit for regulating the duration of said current pulses, a unit for regulating the amplitude of said current pulses, and a unit for indicating the mean value of current intensity, to the patient. The current pulses are applied through electrodes, i.e. attached in the patient's forehead area, and an anode, secured in the neck area, below the mastoids.

4 Claims, 8 Drawing Figures

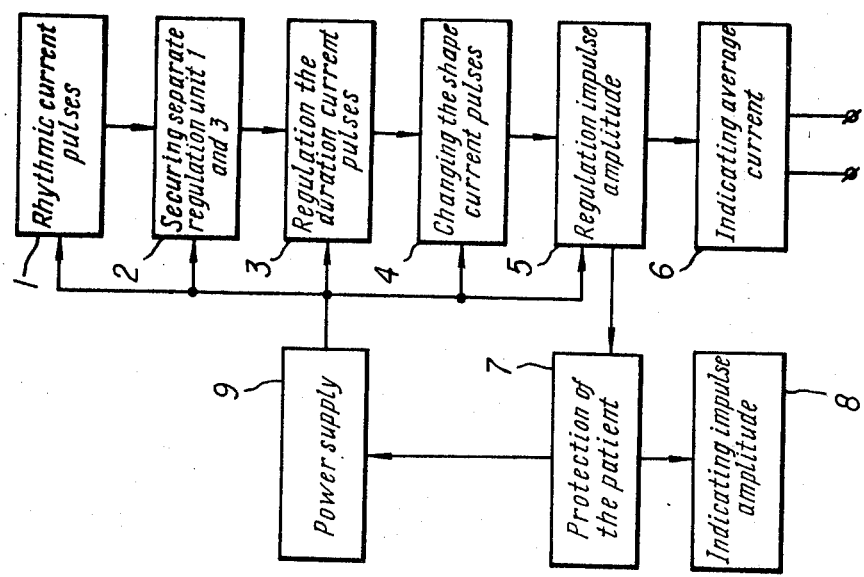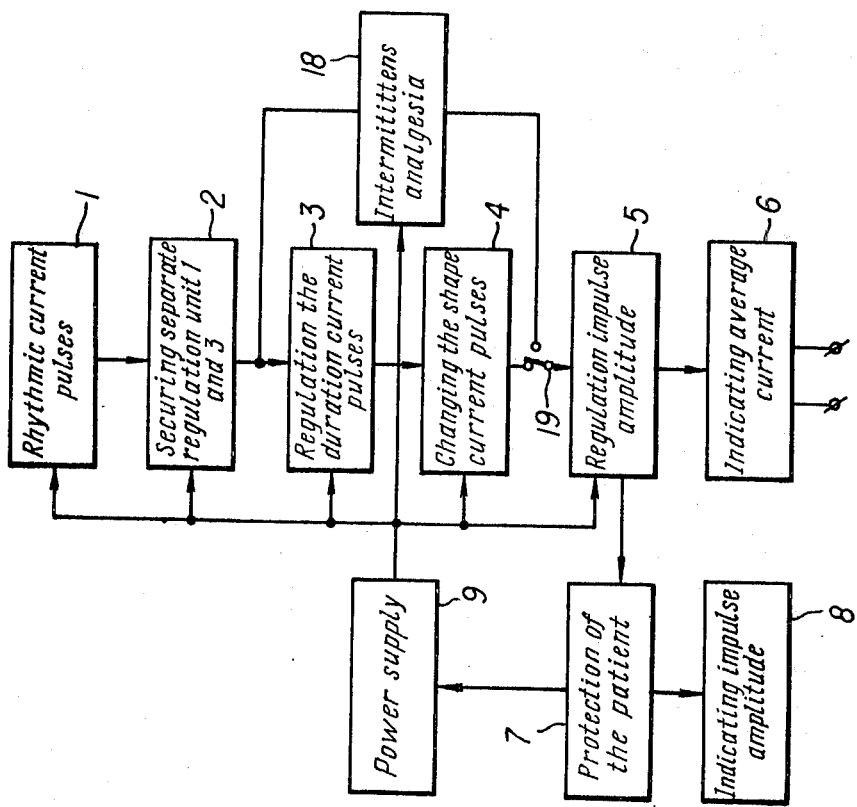

APPARATUS FOR CURRENT PULSE ACTION UPON CENTRAL NERVOUS SYSTEM

This is a continuation of application Ser. No. 510,624 filed Sept. 30, 1974, now abandoned.

BACKGROUND OF THE INVENTION

The present invention relates to medical equipment and, more particularly, to apparatus for current pulse action upon the central nervous system to replace psychotherapeutic medicines, tranquilizers, and general anesthetics.

Recent experimental and clinical studies have shown that the attainment of the second level of the first stage of general electro-anesthesia provides optimum conditions for self-regulation of the cerebrum with subsequent regulation of vital functions of the human organism.

The experience accumulated by today's medicine makes it possible to use the apparatus of this invention to achieve, in clinical conditions, the second level of the first stage of general electro-anesthesia for the prevention and treatment of light and moderate nephropathy, for the prevention of severe nephropathy and uterine action disorders in the course of delivery, and, finally, for raising the pain threshold in the course of preparing expectant mothers for childbirth.

With the start of regular birth-throes, the second level, of the first stage of general anesthesia is employed to give a parturient a respite and replace pharmaceuticals used in cases of uterine inertia.

After alleviating the uterine inertia by attaining the second level of the first stage of general electro-anesthesia, the current pulse action is repeated to intensify uterine activity. The second level of the first stage of general electro-anesthesia may be employed in childbirth to anesthetize labor pains through intermittent analgesia. In operative gynecology the second level of the first stage of general electro-anesthesia is employed to relieve the emotional stress in the course of preparing a patient for an operation, and as an intensified therapy means during the postpartum period.

The proposed apparatus may also be employed for electric sleep treatment and for electrotonising the uterus.

The information obtained at present as to the clinical effectiveness of the second level of the first stage of general electro-anesthesia does not exclude the possibility of employing the proposed apparatus in those fields of gynecology and maieutics where there is the necessity to replace pharmaceuticals by physical means to regulate the functional state of the central nervous system.

There is known an apparatus for current pulse action upon the central nervous system. In this apparatus, which is used for sleep therapy, current pulses are applied to a patient via electrodes, i.e. a cathode and an anode that are attached to the patient's head. Said current pulses are applied from a unit for rhythmic current pulse action upon the central nervous system via a unit for regulating the amplitude of said current pulses, and a unit for indicating the mean value of current intensity, respectively. The sending of the pulses is stopped by the patient protection unit when the current pulse action level is in excess of a preselected value.

The foregoing apparatus acts upon the central nervous system of a patient by square current pulses through electrodes (an anode and a cathode) attached to the patient's head. Said pulses are sent by the rhythmic current pulse action unit which performs the function of a rhythmic irritant to induce sleep in treating different diseases. At the same time the depth of sleep is regulated by varying the output voltage at the points where the electrodes are applied; for this purpose, provision is made for said patient protection unit which comes into action when the current characteristics are in excess of preselected values or in the case of a malfunction of the apparatus.

The rhythmical action unit of said known apparatus comprises a multivibrator with collector base capacitive couplings. This unit ensures a pulse duration of 1.0 to 2 msec in the frequency range of 2 to 25 Hz, and of 0.4 to 1.0 msec in the range of 25 to 130 Hz.

The unit for indicating the mean current intensity value comprises a milliammeter connected directly to the patient.

The patient protection unit comprises an electromechanic relay which is tripped in the case of increased voltage or a fault in the apparatus.

The above circuit layout of the current pulse rhythmic action unit accounts for the fact that it can only be used for sleep therapy in treating different diseases, without making it possible to rapidly and painlessly attain the second level of the first stage of general electro-anesthesia.

The design of the known apparatus described hereinabove is such that the current pulse action in sleep therapy can only be intensified by regulating the output voltage.

SUMMARY OF THE INVENTION

It is an object of the present invention to expand the sphere of application and raise the effectiveness of the proposed apparatus for current pulse action upon the central nervous system.

It is another object of the present invention to provide an apparatus for current pulse action upon the central nervous system, which makes it possible to attain the second level of he first stage of general electro-anesthesia in a patient without causing side effects, as well as to ensures selective action upon different organisms.

The foregoing and other objects of the present invention are attained by providing an apparatus for current pulse action upon the central nervous system, in which apparatus current pulses are applied to a patient, through electrodes, i.e. a cathode and an anode attached to the patient's head, from a unit for rhythmic current pulse action upon the central nervous system via a unit for regulating the amplitude of said current pulses, and a unit for indicating the mean current intensity value, respectively. The sending of said pulses being stopped by a patient protection unit if the amplitude of said current pulses is in excess of a preselected value. The cathode is attached, according to the invention, in the forehead area of the patient, said anode being attached in the patient's neck area, below the mastoids, in order to produce in the central nervous system the second level of the first stage of general electro-anesthesia. The apparatus also including a unit for regulating the duration of said current pulses. The input of this unit is electrically connected to said unit for rhythmic current pulse action upon the central nervous system, whereas its output is connected to said unit for regulating the amplitude of said current pulses, which makes it possible to attain the second level of the first stage of general electro-anesthesia without causing any side effects in the patient.

It is preferred, according to the invention, that the proposed apparatus be provided with a unit for changing the shape of said current pulses acting upon the central nervous system, whose input would be connected to the output of the unit for adjusting the duration of said current pulses, and its output, to the input of the unit for adjusting the amplitude of said current pulses, which would make it possible to attain the second level of the first stage of general electro-anesthesia in weak patients and children.

It is also preferred that the apparatus according to the invention be provided with a unit for indicating the amplitude value of said current pulses. The input would be connected to the output of said patient protection unit.

It is advisable that the proposed apparatus include a unit for securing isolated regulation of unit 1 and 3. The input of this unit would be connected to the output of the unit for rhythmic current pulse action upon the central nervous system, and its output, to the input of the unit for regulating the duration of said current pulses, which would make it possible, in the course of attaining the second level of the first stage of general electro-anasthesia, to effect a selective approach to every patient.

It is desirable, in accordance with the invention that the unit for adjusting, the amplitude of said current pulses of the proposed apparatus be constructed in the form of a voltage generator, which would make it possible to maintain the second level of the first stage of general electro-anesthesia irrespective of changes in the functional state of the central nervous system of a patient.

The apparatus of the present invention for current pulse action upon the central nervous system provides for the employment in clinical medicine of general electro-anesthesia equipment to replace psychotherapeutic medicines, tranquilizers, and general anesthetics. Modern anesthesiology teaches that absence of a pathological reaction to an operational trauma, the regulation of vital systems of the organism during a surgical intervention and after the operation, as well as in the case of a parturient suffering from throbbing pain in the course of delivery, are all ensured by the central nervous system as early as upon the attainment of the second level of general anesthesia and electro-anesthesia (cf. D. Artusio's classification).

Clinical and experimental studies have revealed that general electro-anesthesia brings about a general physiological reaction on the part of the organism, in which process the dominant role is played by the self-regulation ability of the cerebral cortex.

The apparatus of the present invention makes it possible to employ, with due regard for the state of the patient and the functional peculiarities of his or her nervous system, the second level of the first stage of general electro-anesthesia, at a value which is optimum for the prosesses of self-regulation of the cerebrum in accordance with the phase state of the central nervous system.

The foregoing distinctive features of the proposed apparatus substantially expand the sphere of its application and make it possible to regulate the state of the central nervous system in different fields of clinical medicine. The circuit layout of the proposed apparatus makes it possible to employ the second level of the first stage of general electro-anesthesia for treating weak patients and children by changing the shape of current pulses, taking into consideration specific reactions of each patient to changes in the repetition frequency and duration of pulses, and maintain a stable level on the current pulse action irrespective of impedance variations at the points where the electrodes are applied to the patient's head, with different functional states of the cerebral cortex.

BRIEF DESCRIPTION OF THE DRAWINGS

Other objects and advantages of the present invention will become more apparent from the following detailed description of exemplary embodiments thereof to be read in conjunction with the accompanying drawings, wherein:

FIG. 1 is a block diagram of an apparatus for current pulse action upon the central nervous system, in accordance with the invention;

FIG. 7 is another version of the block diagram of the apparatus according to the invention and;

DESCRIPTION OF THE PREFERRED EMBODIMENTS

Figure 4:
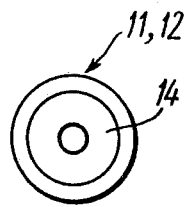
FIG. 4 is a view taken along arrow A of FIG. 3.

The apparatus for current pulse action upon the central nervous system according the present invention is described with reference to an embodiment thereof intended to act upon the central nervous system for treatment and anesthesia in practical maieutics.

Referring now to the attached drawings, the proposed apparatus for current pulse action upon the central nervous system comprises, in accordance with the invention, the following series connected units: a unit 1 (FIG. 1) for generating rhythmic current pulses for action upon the central nervous system; a unit 2 for securing isolated regulation of units 1 and 3, said unit 2 being intended to effect an individual approach to every patient upon reaching the second level of the first stage of general electro-anesthesia in the central nervous system of the patient; a unit 3 for regulating the duration of said current pulses, said unit 3 being intended to produce the second level of the first stage of general electro-anesthesia without causing any side effects in the patient; a unit 4 for changing the shape of said current pulses, said unit 4 being intended to produce the second level of the first stage of general electro-anesthesia in weak patients and children; a unit 5 for adjusting the amplitude of said current pulses; and a unit 6 for indicating the mean current intensity value. The proposed apparatus also includes a patient protection unit 7 to prevent the amplitude of said current pulses from exceeding a preselected magnitude. The input of unit 7 is connected to a second output of the unit 5 for adjusting the amplitude of said current pulses. One output of said unit 7 is connected to a unit 8 for indicating the amplitude value of said current pulses, and its other output is connected to a power unit 9 which is connected, in turn, to an input of the unit 1 for rhythmic current pulse action upon the central nervous system, and to second inputs of the units 2, 3, 4 and 5.

Figure 3:
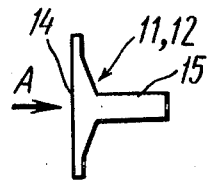
FIG. 3 shows an electrode of the claimed apparatus (side view)
Figure 2:
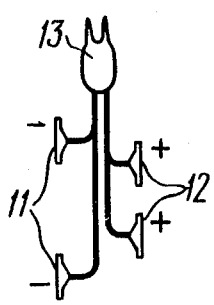
FIG. 2 shows electrodes of the claimed apparatus (general view)
Figure 6:
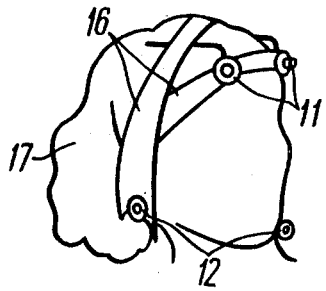
FIG. 6 shows the same mask on a patient's head.
Figure 5:
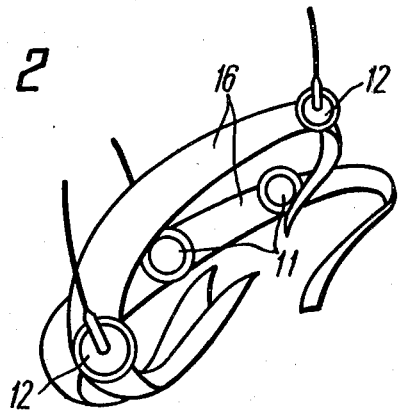
FIG. 5 shows the mask of the claimed apparatus (general view)

Connected to an output 10 (shown in FIG. 1 as two terminals) of the unit 6 for indicating the mean current intensity value, and the aid of a plug 13 (FIG. 2), are electrodes in the form of a bifurcated cathode 11 (FIG. 2) and a bifurcated anode 12. Each of said electrodes, i.e. the cathode 11 and the anode 12 (FIGS. 3 and 4), respectively, comprises a concave disc 14 provided with a conductor 15 (FIG. 3). Said electrodes, i.e. the cathode 11 (FIG. 5) and the anode 12, are attached to rubber bands 16 which make up a mask for tightly fitting a patient's head 17 (FIG. 6). The cathode 11 is attached in the forehead area of the patient, whereas the anode 12 is attached in the neck area, below the mastoids, in order to produce in the central nervous system said second level of the first stage of general electro-anesthesia.

There may be another embodiment of the proposed apparatus for current pulse action upon the central nervous system to be used for delivery anesthetization, which apparatus includes a unit 18 (FIG. 7) to produce intermittent analgesia (from throe to throe) in the course of childbirth. This unit 18 is connected to the unit 2 for securing isolated regulation of the current pulses. In the latter embodiment of the invention the intermittent analgesia unit 18 and the unit 4 for changing the shape of the current pulses are connected to the unit 5 for regulating the amplitude of the current pulses by means of a switch 19.

Figure 8:
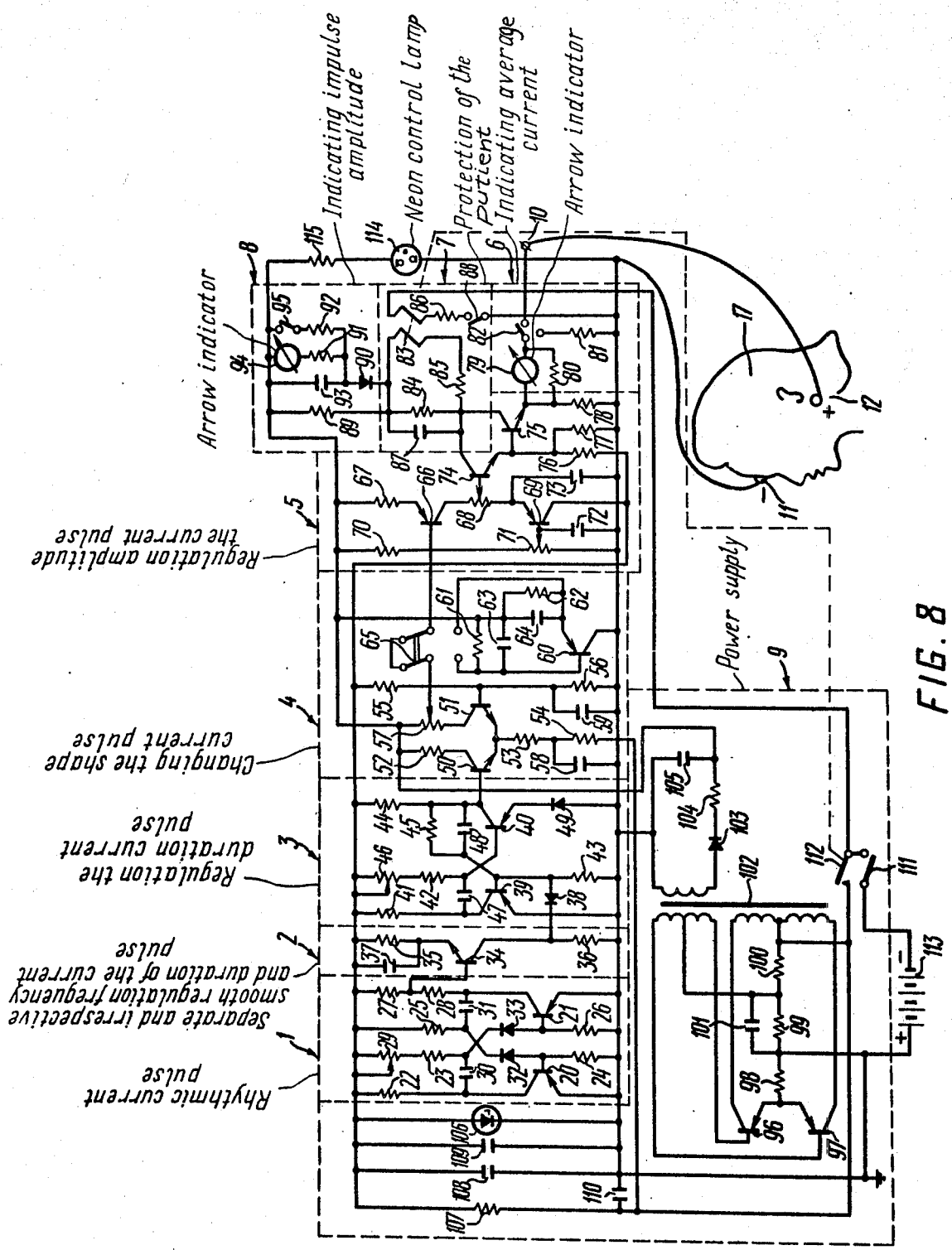
FIG. 8 is a schematic diagram of the apparatus of FIG. 1.

FIG. 8 is a schematic diagram of both the apparatus of FIG. 1 and that of FIG. 7. In both embodiments the units 1 through 9 are identical.

The unit 1 (FIG. 8) for rhythmic current pulse action upon the central nervous system preferrably comprises a multivibrator with collector-base capacitive couplings, consisting of transistors 20 and 21, resistors 22, 23, 24, 25, 26, 27 and 28, a regulable resistor 29, capacitors 30 and 31, and diodes 32 and 33.

The regulable resistor 29 is used to regulate the pulse repetition frequency within a preselected range. At the junction of the resistors 27 and 28, an output of the unit 1 is connected to the base of a transistor 34 of the unit 2 for securing isolated regulation of units 1 and 3.

The unit 2 is constructed, according to the invention, as a differentiating cascade comprising the transistor 34, resistors 35 and 36, and a capacitor 37.

The output of the unit 2, which is the collector of the transistor 34, is coupled via a diode 38 of the unit 3 for regulating the current pulse duration to the base of a transistor 39 of that unit.

The circuitry of the unit 3 is that of a start-stop multivibrator with collector-base capacitive couplings, and comprises transistors 39 and 40, resistors 41, 42, 43, 44 and 45, a regulable resistor 46, capacitors 47 and 48, and diodes 38 and 49. The resistor 46 serves to regulate the current pulse duration within preselected limits.

The output of the unit 3, which is the collector of the transistor 40, is connected to the base of a transistor 50 of the unit 4 for changing the shape of the current pulses.

The unit 4 comprises a first square pulse former and a former of pulses with an exponential trailing edge. The first former consists of as a differential amplifier comprising transistors 50 and 51, resistors 52, 53, 54, 55 and 56, a regulable resistor 57, and capacitors 58 and 59. The second former comprises a transistor 60 provided with a common collector, resistors 61 and 62, and capacitors 63 and 64. Pulse shape selection is done with the aid of a switch 65.

The regulable resistor 57 serves to maintain a constant amplitude irrespective of a change in the pulse shape. The output of the unit 4 is coupled via the contacts of the switch 65 to the base of a transistor 66 of the unit 5 for regulating the current pulse amplitude.

The unit 5 for regulating the current pulse amplitude is constructed as a voltage generator, which makes it possible to maintain, irrespective of the functional state of the central nervous system of the patient, the second level of the first stage of general electro-anesthesia. Said voltage generator comprises the transistor 66, which is provided with a common emitter, a resistor 67, a regulable resistor 68, a transistor 69 provided with a common collector, a resistor 70, a regulable resistor 71, capacitors 72 and 73, transistors 74 and 75, and resistors 76, 77 and 78.

The output of the unit 5, which is the emitter of the transistor 75, is connected to an input of the unit 6 for indicating the mean current intensity value.

The unit 6 comprises a measuring instrument 79, resistors 80 and 81, and a switch 82 which serves to calibrate the measuring instrument. Connected to the output 10 of said unit 6, with the aid of the plug 13 (FIG. 2), are the electrodes, i.e. the anode 12 (FIG. 8) and the cathode 11. The latter is grounded.

The patient protection unit 7 (FIG. 8) comprises a relay 83, resistors 84, 85 and 86, a capacitor 87, and a switch 88 for setting the relay 83 in the initial position. The patient protection unit 7 is connected to the collector circuit of the transistors 74 and 75 of the unit 5. The output of the unit 7 is connected to the input of the unit 8 for indicating the mean current intensity value.

The circuitry of the unit 8 is that of a peak detector. The unit 8 comprises a resistor 89, a diode 90, resistors 91 and 92, a capacitor 93, a measuring instrument 94, and a switch 95. The switch 95 serves for resetting the pointer of the measuring instrument 94.

The power unit 9 comprises a voltage changer, a rectifier and a voltage stabilizer. The voltage changer comprises aro transistors 96 and 97, resistors 98, 99 and 100, a capacitor 101, and a transformer 102. Said rectifier comprises a diode 103, a resistor 104, and a capacitor 105. The voltage stabilizer comprises a silicon stabilitron 106, a resistor 107, and capacitors 103, 109 and 110.

A switch 111 is intended to apply the supply voltage to the voltage stabilizer and the voltage changer. A contact 112 of the relay 83 serves to cut off the supply voltage generated by a power source 113 from the voltage changer if current characteristics are in excess of preselected values. The presence of a high voltage is indicated by the glow of a neon lamp 114 which is connected to a resistor 115.

According to the second embodiment of the invention the unit 18 (FIG. 7) for intermittent analgesia (from throe to throe) in the course of delivery preferably comprises an integrated microcircuit such as a j − k flip-flop.

OPERATION

The apparatus of FIG. 1 for current pulse action upon the central nervous system operates as follows.

The mask made up of the rubber bands 16 is fitted over the patient's head 17 (FIG. 6). The cathode 11 is attached in the forehead area of the patient, and the anode 12, in the neck area, below the mastoids, in order to produce the second level of the first stage of general electro-anestheisa.

A series of square pulses is generated at the output of the unit 1 (FIG. 8) for rhythmic current pulse action upon the central nervous system. The repetition frequency of said pulses is varied between 100 Hz and 7 kHz with the aid of the regulable resistor 29. From the output of the unit 1 said series of pulses is applied to the unit 2 for securing isolated regulation of units 1 and 3 the pulse repetition frequency and duration. Formed at the output of the unit 2 is a series of pulses with a duration of 0.05 msec and a repetition frequency corresponding to that of pulses sent from the unit 1. The unit 2 provides for a selective approach to every patient upon producing in the central nervous system the second level of the first stage of general electro-anesthesia.

From the output of the unit 2 the series of pulses is applied via the diode 38 to the input of the unit 3 for regulating the pulse duration. The regulable resistor 45 regulates the pulse duration, which makes it possible to produce in the central nervous system of the patient the second level of the first stage of general electro-anesthesia without causing any side effects. The pulse signal with a desired duration is applied from the output of the unit 3 to the input of the unit 4 for changing the pulse shape, where the pulse shape is altered with the aid of a switch 65. The latter makes it possible to produce the second level of the first stage of general electro-anesthesia in weak patients and children.

From the output of the unit 4 the series of pulses is applied to the pulse amplitude regulation unit 5 which maintains constant the second level of the first stage of general electro-anesthesia irrespective of changes in the functional state of tthe central nervous system, and which also makes it possible to regulate the pulse amplitude with the aid of the regulable resistor 68.

From the output of the unit 5 the signal is applied to the measuring instrument 79 of the unit 6 for indicating the mean current intensity value, which instrument is used to control the level of general electro-anesthesia. From the output of the unit 6, and via the switch 82, the signal is applied to the anode 12 attached to the patient's head 17 in the neck area, below the mastoids.

the patient protection unit 7, which is connected to the collector circuit of the transistor 75 of the unit 5, disconnects the power unit 9 from the power source 113 with the aid of the contact 112 of the relay 83, which ensures absolute safety of the patient and stops the sending of current pulses to the anode 12 if the current pulse amplitude is in excess of a preselected value.

The output of the unit 7 is connected to the unit 8 for indicating the current pulse amplitude value, which unit 8 measures the amplitude characteristic of the current. In conjunction with the operation of the unit 6, this makes it possible to check the anesthesia level upon attaining the second level of the first stage of general electro-anesthesia.

The operating principles of the apparatus of FIG. 7 is similar to that of the apparatus of FIG. 1.

The difference between the two embodiments lies in the fact that applied to the input of the intermittent analgesia unit 18 (FIG. 7) is a series of pulses from the output of the unit 2, which series has a pulse repetition frequency corresponding to that set in the unit 1. At the output of the unit 18 a series of square pulses is formed with an on-off time ratio equal to 2. The switch 19 is used to bring into play the unit 18 when there is present the necessity to perform anesthesia with the start of uterine action.

The sequence of operations necessary to produce the second level of the first stage of general electro-anesthesia with the aid of the apparatus for current pulse action upon the central nervous system of FIG. 1 is as follows: The electrodes are applied onto the patient's head, and pulse repetition frequency is set in the unit 1 between 100 Hz and 7 kHz. With the aid of the unit 2 the isolated regulation of units 1 and 3 is secured is carried out, which ensures a selective approach to every patient. The unit 3 regulates the current pulse action to achieve the second level of the first stage of general electro-anesthesia without causing side effects in the patient. The unit 4 changes the rectangular shape of the acting current pulses to a triangular form which makes it possible to attain the second level of the first stage of general electro-anesthesia in weak patients and children. The unit 5, which is constructed as a voltage generator, serves to maintain stable the second level of the first stage of general electro-anesthesia irrespective of changes in the functional state of the central nervous system. That is followed by selecting the current pulse amplitude.

The above sequence of operations is performed in attaining the second level of the first stage of general electro-anesthesia with the aid of the apparatus of FIG. 7 employed for delivery anesthetizing.

In each particular case, the absolute values of different pulse action parameters may be different. Clinical symptoms are then checked, which characterize the optimum self-regulation level in the central nervous system and the establishment of a stable vegetative equilibrium (stabilized pulse, breathing and blood pressure).

At present, substantial clinical experience has been accumulated (some 600 observations) in employing the second level of the first stage of general electro-anesthesia in different areas of maieutics and gynecology. In order to rule out the effects of pharmaceuticals upon the organism of the expectant mother and the fetus in cases of functional neuroses and emotional stresses, an expectant mother is prepared for delivery by being subjected to current pulse action upon the central nervous system in clinical conditions. The category of females for whom such preparation is indicated includes expectant mothers who have previously suffered a birth failure, those suffering from gynecological and somatic diseases, and those passing through an early stage of late toxemia of pregnancy.

As far as hospitalized patients are concerned, the second level of the first stage of general electro-anesthesia is employed for treating light and moderate nephropathy and for the prevention of severe nephropathy.

The second level of the first stage of general electro-anesthesia is produced in expectant mothers two weeks before the delivery to prevent disorders in uterine action. A total of 300 cases was observed, with the treatment being 85 to 90 percent effective.

Current pulse action treatment is employed in the course of delivery to replace pharmaceuticals which are normally used to give a respite to the parturient or prevent a painful delivery.

In cases of uterine inertia during the latent and active phases of delivery current pulses are successfully employed to regulate uterine activity (200 cases). This has been corroborated by statistical processing of information on contractions of the body and the lower part of the uterus (hysterography).

Research in the field of maieutics was accompanied by studies of the biological activity of the cerebrum and the cardiovascular system of the mother and the fetus.

In cases of late toxemia of pregnancy, current pulse action normalizes the electric activity of the cerebrum and improves the cerebral circulation (rheoencephalography).

Pulse currents improve cardiac action of the fetus through facilitating the circulation in the uterus and dilating the vessels (electrohonocardiography of the fetus, rheography of the uterus).

As an intensive therapy means, the second level of the first stage of general electro-anesthesia is employed duirng the postoperative period to regulate vital functions of the organism (narcosis) and replace preparations of the morphine group (100 cases).

Contraindications to current pulse treatment are severe somatic disorders requiring a special course of treatment, organic disorders of the nervous system, the impossibility of spontaneous delivery, placenta praevia, ablatio placentac, the danger of hysterorrhexis, preeclampsia, eclampsia, coma, and mental aberrations.

Current pulse treatment must not be combined with atropine, tranquilizers, and non-inhalation anesthesia. The abovecombinations may lead to uncontrolled anesthesia which may reach the surgical level.

It is recommended that current pulse action should go along with pypolphen, petidine (one time only), and nitrous oxide with oxygen.

The apparatus of the present invention can be massproduced with the aid of micromodules and printed circuits.

The proposed apparatus is absolutely safe in operation, portable, autonomous, and easy to handle, which factors promise its wide application in all fields of medicine. the apparatus of this invention may find extensive application in a portable version to be used in rural areas or in cases when a parturient is delivered of a child at home. The apparatus may be handled by medium-level medical personnel, provided that the general supervision is done by a doctor. The apparatus of the present invention may be used in field conditions to combat shock before qualified medical aid is available. In cases of oxygen deficiency (submarines, underground installations, high altitudes) the apparatus of the present invention makes it possible to treat functional disorders of the central nervous system without resorting to pharmaceuticals whose removal from the organism is much slower than normal in the abovementioned conditions.

What is claimed is:

1. An apparatus for current pulse action upon the central nervous system, comprising in combination: a first means for rhythmic current pulse action upon the central nervous system of a patient, said first means having an input and an output; second means for regulating the duration of said current pulses, said second means attains in the central nervous system the second level of the first stage of general electro-anaesthesia without causing any side effects in said patient, and which has a first input and a second input and one output, said second means being electrically connected with its first input to said output of said first means; third means for regulating the amplitude of said current pulses, said third means having a first input and a second input, a first output and a second output, said third means having its first input electrically connected to said output of said second means; fourth means for indicating the mean current intensity value, said fourth means having an input and an output and being connected with its input to the first output of said third means; anode means connected to said output of said fourth means for attachment to the neck area of said patient, just under the mastoids; cathode means connected to said output of said fourth means for attachment to the forehead area of said patient; patient protection means having one input and two outputs, whose first output is connected to a power-supply, and whose second output is connected to fifth means for indicating the amplitude current value; said power-supply having an input and an output, said output connected to said input of said first means and said second inputs of said second and third means, said input connected to said first output of said patient protection means for disconnecting said power-supply from said first, second and third means when the amplitude of the acting current pulses exceeds a predetermined value.

2. An apparatus as claimed in claim 1, further comprising: sixth means for changing the shape of the acting current pulses, said sixth means for attaining the second level of the first stage of general electro-anaesthesia in weak patients and children and having a first input, a second input, and one output, and being connected with its first input to said output of said second means, while its second input is connected to said output of said power-supply and its output is connected to the first input of said third means.

3. An apparatus as claimed in claim 1, further comprising seventh means for securing isolated regulation of said first and second means for assuring an individual approach to each patient as the second level of the first stage of general electro-anaesthesia is achieved, said seventh means having a first and a second input, said first input being connected to said output of said power-supply, said second input being connected to said output of said first means, while said output is connected to the first input of said second means.

4. An apparatus as claimed in claim 3, wherein said third means comprises voltage generator means for maintaining the second level of the first stage of general electro-anaesthesia when the functional state of said central nervous system of said patient varies.

* * * * *